United States Patent
Zobele

(10) Patent No.: US 6,827,286 B2
(45) Date of Patent: Dec. 7, 2004

(54) DIFFUSER DEVICE FOR DIFFUSING SOLUTIONS

(75) Inventor: Franco Zobele, Trento (IT)

(73) Assignee: Zobele Holding SpA, Trento (IT)

(*) Notice: Subject to any disclaimer, the term of this patent is extended or adjusted under 35 U.S.C. 154(b) by 0 days.

(21) Appl. No.: 10/417,753

(22) Filed: Apr. 17, 2003

(65) Prior Publication Data
US 2004/0021001 A1 Feb. 5, 2004

(30) Foreign Application Priority Data
Aug. 1, 2002 (IT) .................................. MI2002A1729

(51) Int. Cl.⁷ .................................................. A24F 25/00
(52) U.S. Cl. ........................................ 239/44; 122/366
(58) Field of Search ........................... 239/44; 122/366; 392/386, 392, 394, 395, 403, 412; 126/358.1, 350.2, 236.01, 96

(56) References Cited

U.S. PATENT DOCUMENTS

| | | |
|---|---|---|
| 6,278,840 B1 | 8/2001 | Basagañas Millan |
| 6,446,583 B2 * | 9/2002 | Vieira ..................... 122/366 |
| 6,478,440 B1 * | 11/2002 | Jaworski et al. ............. 362/96 |
| 6,661,967 B2 * | 12/2003 | Levine et al. .............. 392/395 |
| 2001/0020450 A1 | 9/2001 | Vieira |

FOREIGN PATENT DOCUMENTS

| | | |
|---|---|---|
| EP | 0 943 344 A1 | 9/1999 |
| EP | 0 962 132 A1 | 12/1999 |
| EP | 1 064 957 A1 | 1/2001 |
| WO | WO 98/19526 | 5/1998 |

* cited by examiner

*Primary Examiner*—Gene Mancene
*Assistant Examiner*—Thach H. Bui
(74) *Attorney, Agent, or Firm*—Merchant & Gould

(57) ABSTRACT

A diffuser device (100) for diffusing solutions comprises a refill (6) containing the solution to be diffused, a wick (7) disposed partially inside the refill (6) to absorb the solution, a heater (1) coupled to the refill (6) and to the wick (7) and comprising a resistance (8), able to increase in temperature when crossed by a current, for heating the wick (7) and supply means (5) able to electrically supply the resistance (8), the resistance (8) being supported by a support (20) mounted movably in the heater (1) to be able to pass, by manual operation, from a position distal to the wick (7) wherein minimum heating of the wick occurs to a position proximal to the wick wherein maximum heating of the wick occurs.

16 Claims, 4 Drawing Sheets

DIFFUSER DEVICE FOR DIFFUSING SOLUTIONS

The present invention refers to a diffuser device for diffusing solutions and in particular to a diffuser device of the type with a heating element and a refill with an evaporating wick for diffusing solutions containing active principles, such as deodorants, insecticide substances, disinfectants and the like.

Various types of diffuser devices comprising an electric heater provided with an electrical plug for connection to an electrical socket so as to supply an electric resistance which heats up are available on the market at present. The heater is coupled to a refill containing a solution and provided with an evaporating wick which, when heated through contact with the resistance, diffuses the solution.

Diffuser devices of the prior art present some drawbacks.

One drawback is represented by the difficulty in regulating the amount of substance diffused. In fact, when the electrical resistance of the diffuser device is crossed by a current, the wick is heated in a constant and uniform manner and, according to the heating of the wick, the essence is diffused in an uncontrolled manner into the air. There are devices able to regulate the amount of essence diffused into the air; however, said devices are particularly complex and composed of a high number of parts.

An object of the present invention is to overcome the drawbacks of the prior art, providing a diffuser device that is practical for the user and at the same time versatile and able to adapt to various types of refills and electrical sockets.

Another object of the present invention is to provide such a diffuser device that is economical and simple to realise.

The diffuser device according to the invention comprises a refill containing the solution to be diffused, a wick disposed partially inside the refill to absorb the solution and a heater coupled to the refill and to the wick. Inside the heater is disposed at least one resistance element able to increase in temperature when crossed by a current to heat the wick and to allow the diffusion of the solution. The diffuser device further comprises supply means able to electrically supply the resistance element.

The peculiar characteristic of the invention is represented by the fact that the resistance element is supported by a support mounted movably inside the heater to be able to pass, by manual operation, from a position distal to the wick, wherein minimum heating of the wick occurs, to a position proximal to the wick, wherein maximum heating of the wick occurs.

From this brief description the advantages of the diffuser device according to the invention are evident. In fact the user, by moving manually the resistance holding support, is able to regulate precisely the amount of heat given off by the resistance to the wick and thus the diffusion of the solution by the wick.

Further characteristics of the invention will be made clearer by the detailed description that follows, referring to a purely exemplary and therefore non limiting embodiment, shown by the appended drawings, in which.

Figure 1:
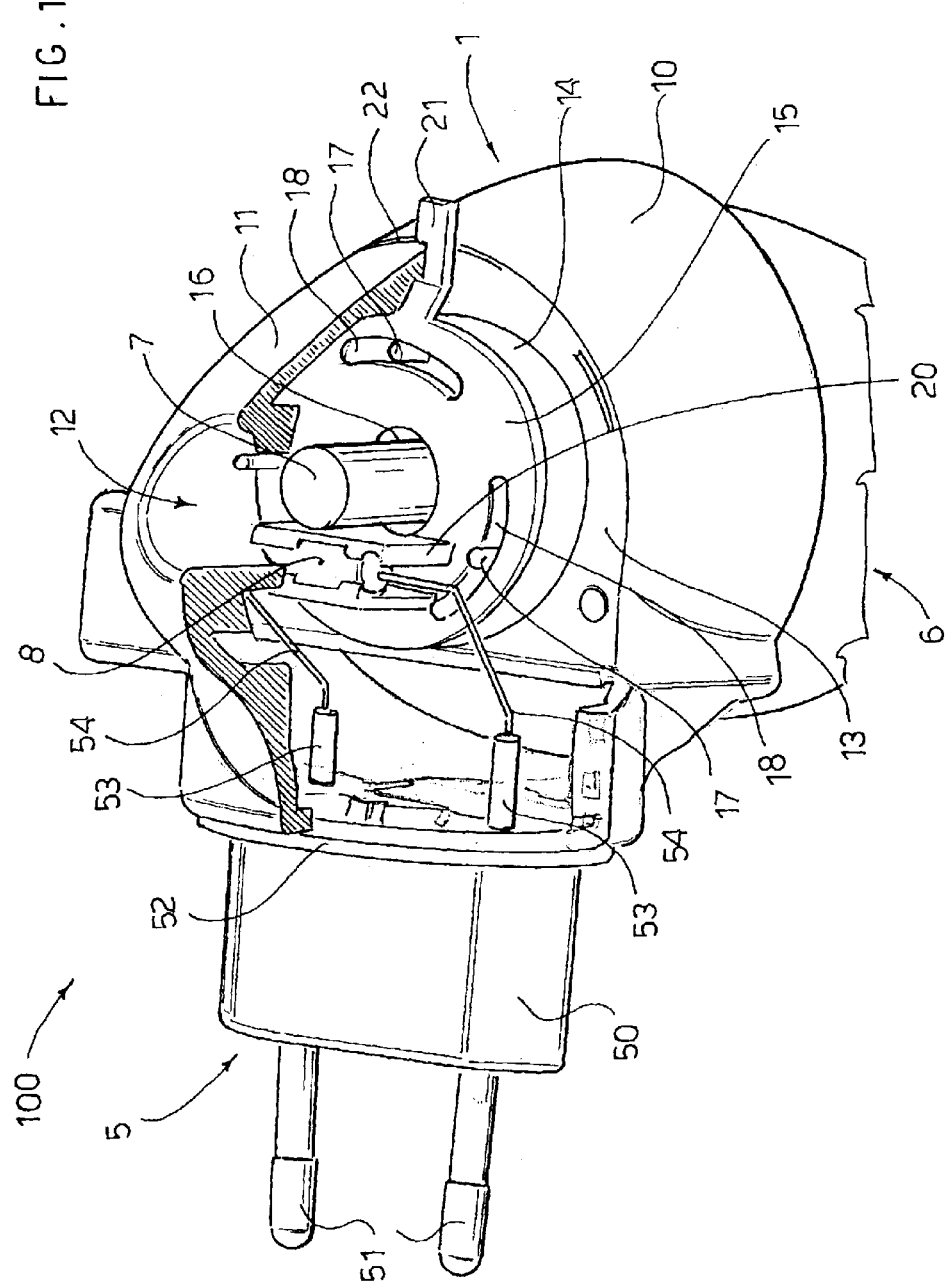
FIG. 1 is a perspective view, illustrating a diffuser device for diffusing solutions according to the invention, wherein the upper shell half of the burner is shown partially in section.

The diffuser device according to the invention, denoted as a whole with reference numeral 100, is described with the aid of the figures. The diffuser apparatus 100 comprises a heater 1, a container or refill 6 coupled to the heater 1 and containing the solution to be diffused, a wick 7 coupled to the heater 1 and partially immersed in the solution inside the refill 6, and an electrical plug 5 coupled to the heater 1, to supply an electrical resistance 8 disposed in the heater 1 to heat the wick 7.

The heater 1 comprises a lower shell half 10 and an upper shell half 11 which can be assembled together so as to define an inner chamber wherein the resistance 8 and one end of the wick 7 are situated. The two shell halves 10 and 11 can be assembled by means of suitable fixing means, such as mortising, heat welding, ultrasound welding, gluing and the like.

The upper shell half 11 of the heater has an axial through hole 12 able to put the chamber defined by the two shell halves into communication with the outside to allow diffusion of solutions into the outside environment. Clearly, instead of or in addition to the axial hole 12, the shell halves 10 and 11 can have slits or slots for diffusion of the solution towards the outside.

The lower shell half has at the top a horizontal supporting plate 13, whereon a cylindrical tang 14 rises. The lower shell half 10 has an axial through hole through which the wick 7 passes. Furthermore, the lower shell half 10 has at the bottom suitable coupling means for coupling to the refill 6 which is in the form of a small bottle.

If the diffuser device 100 is of the refillable type, the refill 6 is removably coupled to the lower shell half 10, for example by screwing or tonguing or snap coupling. If the diffuser device 100 is a disposable one, the container 6 can be irremovably coupled to the lower half shell 10, for example by heat welding, ultrasound welding, gluing or the like.

The wick 7 is substantially cylindrical in shape and has one end immersed in the solution inside the refill 6 and the other end disposed inside the chamber formed by the two shell halves 10 and 11 of the heater. The wick 7 is made of porous material able to absorb the solution contained in the refill 6.

The electrical plug 5 comprises a body 50 having at one-end two pins 51 suitable to be inserted in an electrical socket. In FIG. 1 a plug with cylindrical pins according to the European standard is shown; however, a plug with flat pins according to the American standard could also be provided.

At the other end, the body 50 of the plug ends in a circular plate 52, disposed on a plane at right angles with respect to the axis of the pins 51. The plate 52 of the plug is mounted rotatably between the two shell halves 10 and 11 of the heater. In this manner the heater 1 and refill 6 assemblies can rotate with respect to the plug 5, so as to orient the refill 6 correctly downward, according to the orientation of the socket, which receives the plug 5. In this manner, the solution contained in the refill 6 is prevented from leaking to the outside from the top of the refill.

Behind the circular plate 52 of the plug, inside the chamber defined by the two half shells 10, 11 of the heater, electrical contacts 53 electrically connected to the pins 51 of the plug are provided. The electrical contacts 53 are connected, by means of electrical connecting wires 54, to two terminals 81 of the electrical resistance 8. Clearly, for the sake of safety, metal-conducting parts—such as the electrical contacts 53 of the plug, the conducting wires 54 and the terminals 81 of the resistance—can be covered with insulating sheaths.

In FIG. 1, by way of example, an electrical plug 5 has been shown; however, instead of the electrical plug 5 another source of electrical power, such as—for example—a battery, can be provided to supply the electrical resistance 8.

According to the invention an operating flange 15 in the form of a circular plate is mounted rotatably on the tang 14 of the lower shell half 10. The flange 15 has, in a central position, a through hole 16, which allows the passage of the wick 7.

A support 20 able to support the electrical resistance 8 is provided on the operating flange 15 close to the hole 16. The support 20 is made integral with the operating flange 15. The resistance holding support 20 is in the form of a substantially parallelepiped housing and is preferably made of an electrically insulating, good heat conductor material, so as to protect the resistance 8 from possible short circuits and at the same time ensure good heating of the wick 7.

To improve the clarity, in the figures the resistance-holding support 20 is shown open at the top for inserting the resistance 8, which is disposed parallel to the plane of the flange 15 and at right angles to the axis of the wick 7. However, the resistance holding support 20 can also be closed at the top or made so as to support the resistance in a longitudinal position with the axis substantially parallel to the axis of the wick 7. In any case, for the sake of safety, the resistance and the terminals 81 of the resistance can be protected with a suitable insulating sheath.

The operating flange 15 has an operating lever 21, which protrudes radially outward so that the user can operate it. The operating lever 21 protrudes from a slot 22 made between the lower shell half 10 and the upper shell half 11 of the heater. In this manner the user, by operating the operating lever 21, can rotate the operating flange 15.

Figure 2:
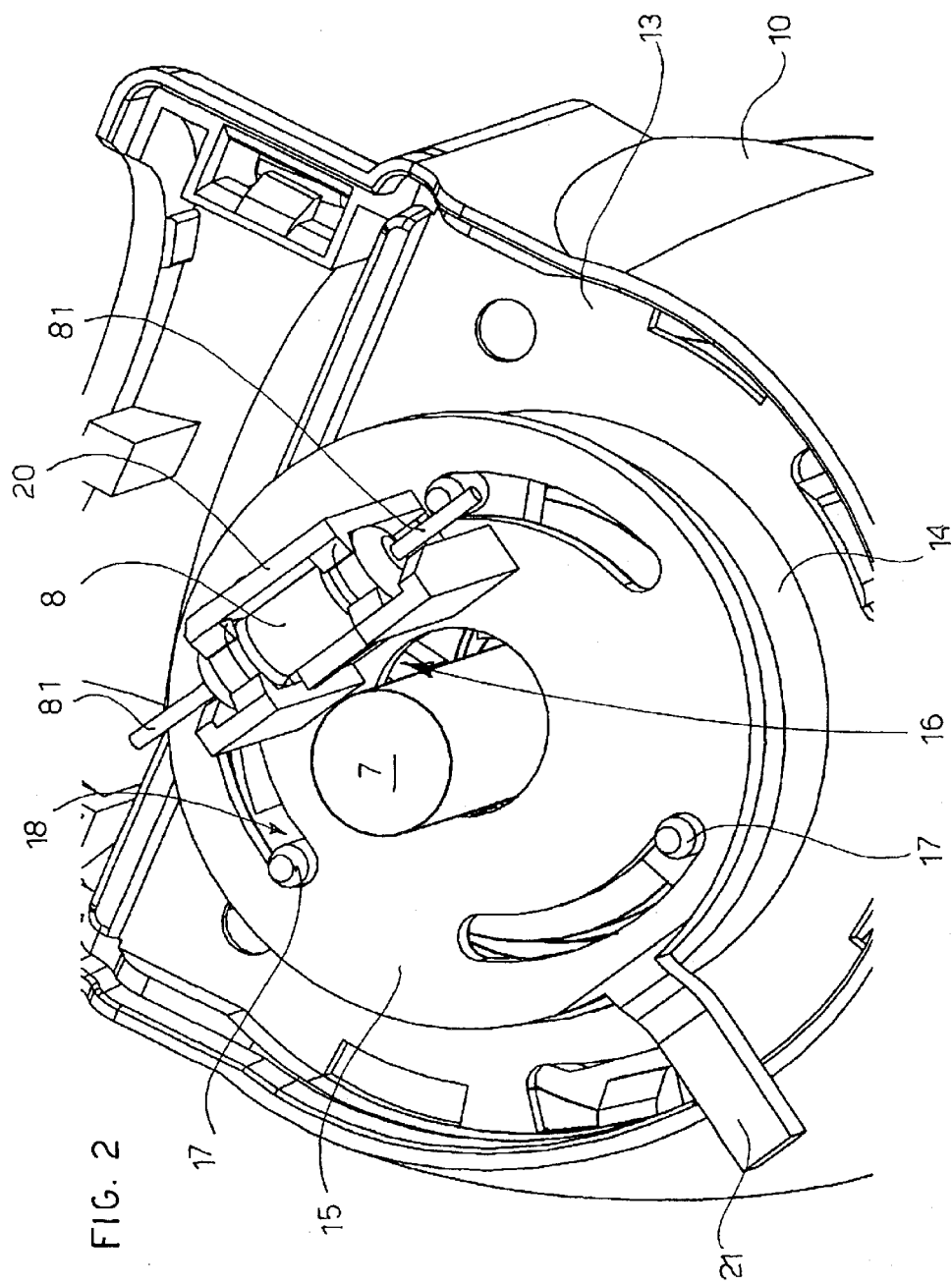
FIG. 2 is a perspective view, enlarged and partially broken off, showing the diffuser apparatus of FIG. 1, wherein, for the sake of clarity, the upper half shell of the heater and the conductor wires connected to the terminals of the electrical resistance have been removed and wherein the electrical resistance is in the distal position of minimum heating of the wick.
Figure 3:
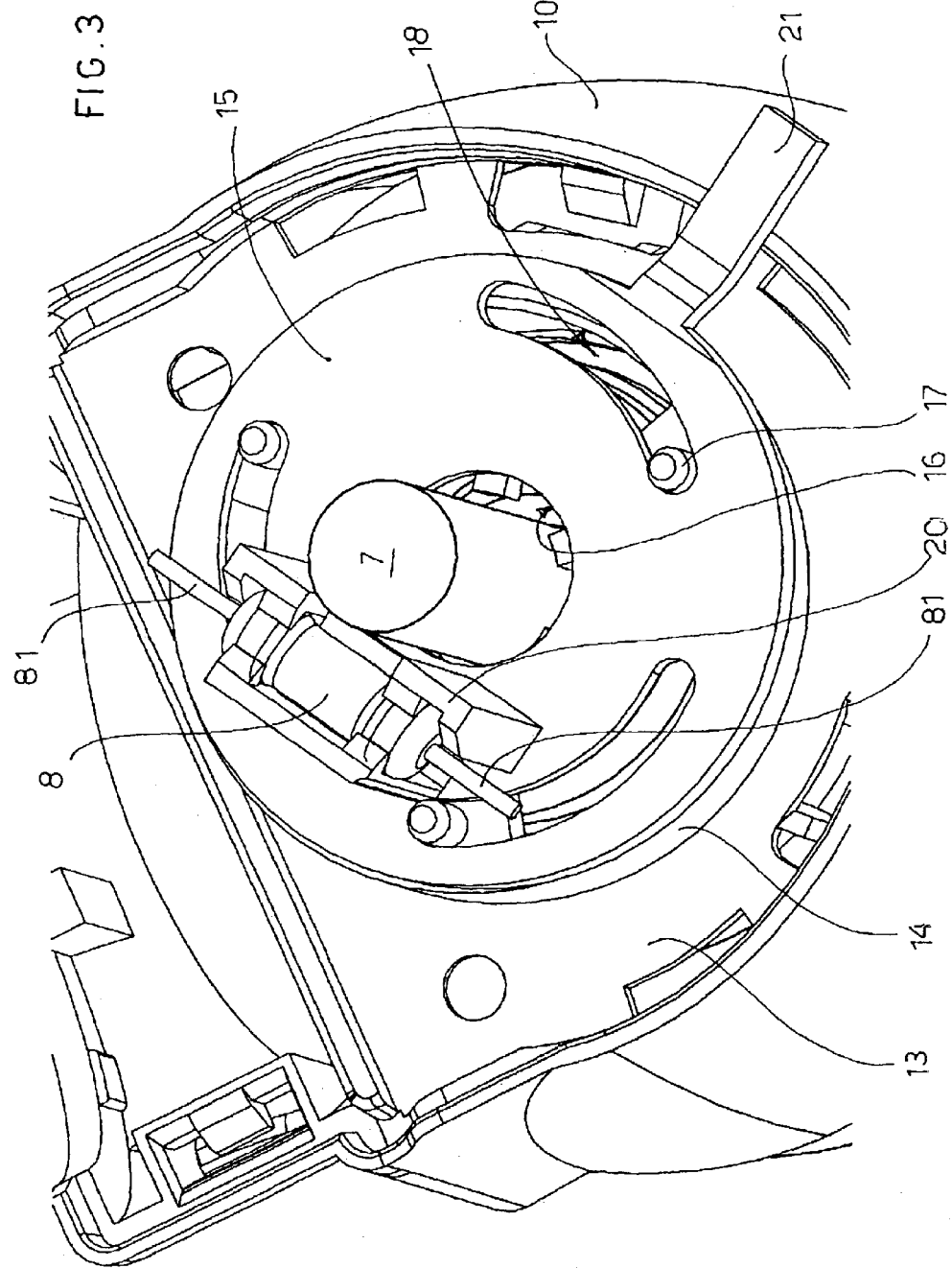
FIG. 3 is a view like FIG. 2, wherein the electrical resistance is in the proximal position of maximum heating of the wick.

It should be noted that a certain gap is left between the outer surface of the wick 7 and the edge of the through hole 16 of the flange. Furthermore, the operating flange 15 is mounted eccentrically with respect to the wick 7. That is to say, when the operating flange 15 is rotated, the resistance holding support 20 makes an eccentric rotation with respect to the wick 7. As a result, the resistance holding support 20 passes from a position of minimum heating, shown in FIG. 2, wherein the resistance 8 is far from the wick 7 to a position of maximum heating, shown in FIG. 3, wherein the resistance 8 is near to the wick 7.

To guide the eccentric rotation of the operating flange 15 with respect to the wick 7, on the tang 14 of the lower shell half 10 there are provided peripheral pins which protrude upwards to engage in respective peripheral slots 18 provided in the operating flange 15. The slots 18 in the flange have a substantially curved shape and act as cams, whilst the pins 17 of the tang of the lower shell half act as cam followers.

In this manner the operating flange 15 can turn on the tang 14 of the lower shell half and said rotation is guided by the pins 17, which slide in the curved slots 18. Consequently, the two ends of the curved slots 18 of the operating flange respectively constitute two stop points for rotation of the operating flange 15.

By way of example, three curved slots 18, disposed peripherally on the operating flange 15 and equidistant from each other have been shown. However, only one curved slot 18 or a number of curved slots different from three can be provided.

In any case, the invention is not limited to the embodiment shown by the appended drawings. In fact other systems which are within the reach of a person skilled in the art—such as guides, slides and the like which allow the resistance 8 to be caused to make a movement relative to the wick 7—can be provided. In this manner the resistance 8 can assume a plurality of positions included in the range between a distal position of the wick wherein minimum heating occurs and a proximal position of the wick wherein maximum heating occurs. As a result, a fine and precise regulation of the amount of solution to be diffused into the air is obtained.

Figure 4:
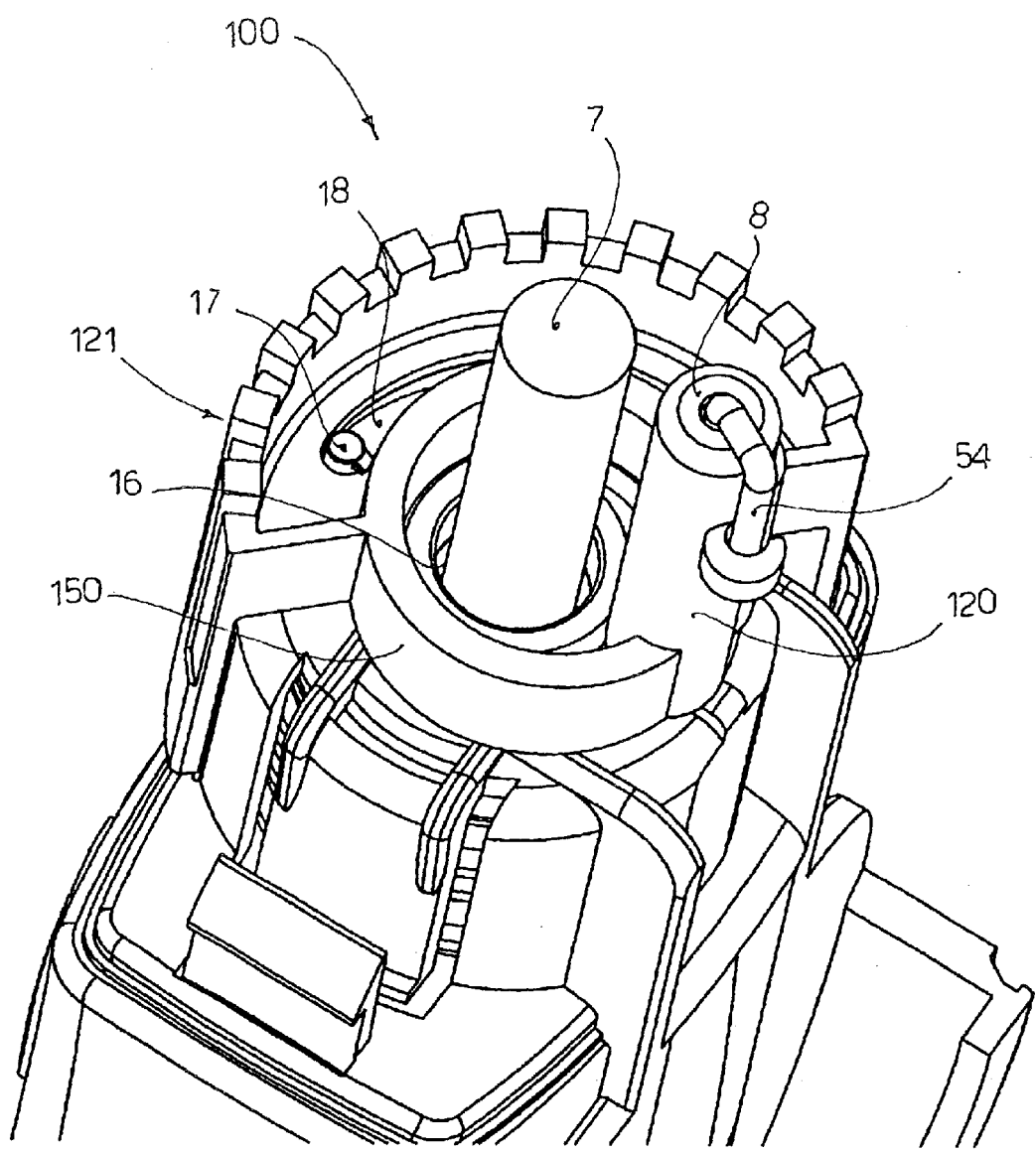
FIG. 4 is a perspective view, enlarged and partially broken off, of a diffuser device for diffusing solutions according to a second embodiment of the invention.

FIG. 4 shows diffuser device 10 according to a second embodiment of the invention, wherein the same elements or those corresponding to already described ones are denoted with the same reference numerals.

In this case the operating flange 15 has only one cam slot 18 engaged by a pin 17 of the tang of the lower shell half of the heater. Thus a circular frame 150, disposed around the hole 16 for the passage of the wick 7, is provided on the operating flange 15. A substantially cylindrical resistance holding support 120, disposed longitudinally with the axis parallel to the axis of the wick, is integrated into the frame 150. An electrical resistance 8 disposed longitudinally with the axis parallel to the axis of the wick is mounted in the resistance holding support 120.

In this second embodiment, in place of the operating lever 21 of the first embodiment, on the peripheral surface of the operating flange 15 a cylindrical ring nut 121—that can be operated in rotation by the user to turn the operating flange—is provided.

The operating flange 15, the frame 150, the resistance holding support 120 and the cylindrical ring nut 121 are preferably made in a single body by injection moulding.

Numerous variations and modifications of detail, which are within the reach of a person skilled in the art, can be made to the present embodiment of the invention without departing from the scope of the invention as expressed by the appended claims.

What is claimed is:

1. A diffuser apparatus for diffusing solutions comprising:
    a container or refill containing the solution to be diffused,
    a wick disposed at least partially inside said container to absorb said solution to be diffused,
    a heater coupled to said container and to said wick and comprising at least one resistance element, able to increase in temperature when crossed by a current, to heat said wick so as to allow diffusion of said solution from said wick,
    supply means able to electrically supply said resistance element, characterised in that said resistance element is supported by a support mounted movably in said heater to be able to pass, by user's manual operation, from a position distal to said wick wherein minimum heating of the wick occurs to a position proximal to said wick wherein maximum heating of the wick occurs, and wherein
    said resistance holding support is mounted eccentrically rotatable with respect to said wick.

2. A diffuser device (100) according to claim 1, characterised in that said resistance holding support is disposed on an operating flange rotatably mounted inside said heater.

3. A diffuser device according to claim 2, characterised in that said resistance holding support is integral with said operating flange.

4. A diffuser device according to claim 2, characterised in that said operating flange has, in a central position, a through hole able to allow the passage of said wick, a certain gap between the outer surface of the wick and the edge of the hole being provided.

5. A diffuser device according to claim 2, characterised in that said operating flange is rotated eccentrically around said wick by means of a cam system.

6. A diffuser apparatus for diffusing solutions comprising:
a container or refill containing the solution to be diffused;
a wick disposed at least partially inside said container to absorb said solution to be diffused;
a heater coupled to said container and to said wick and comprising at least one resistance element, able to increase in temperature when crossed by a current, to heat said wick so as to allow diffusion of said solution from said wick;
supply means able to electrically supply said resistance element, characterised in that said resistance element is supported by a support mounted movably in said heater to be able to pass, by user's manual operation, from a position distal to said wick wherein minimum heating of the wick occurs;
said resistance holding support being mounted eccentrically rotatable with respect to said wick;
said resistance holding support being disposed on an operating flange rotatable mounted inside said heater;
said operating flange being rotated eccentrically around said wick by means of a cam system; and
said operating flange having at least one peripheral curved slot, acting as a cam, able to be engaged by a respective pin integral with said heater and acting as a cam follower.

7. A diffuser device according to claim 2, characterised in that said operating flange has an operating lever (21) protruding radially therefrom to emerge from said heater so as to be able to be manually operated by the user.

8. A diffuser apparatus for diffusing solutions comprising:
a container or refill containing the solution to be diffused;
a wick disposed at least partially inside said container to absorb said solution to be diffused;
a heater coupled to said container and to said wick and comprising at least one resistance element, able to increase in temperature when crossed by a current, to heat said wick so as to allow diffusion of said solution from said wick;
supply means able to electrically supply said resistance element, characterised in that said resistance element is supported by a support mounted movably in said heater to be able to pass, by user's manual operation, from a position distal to said wick wherein minimum heating of the wick occurs;
said resistance holding support being mounted eccentrically rotatable with respect to said wick;
said resistance holding support being disposed on an operating flange rotatably mounted inside said heater;
said operating flange being rotated eccentrically around said wick by means of a cam system; and
said operating flange having integrally in its peripheral surface a cylindrical ring nut operable in rotation by the user.

9. A diffuser apparatus for diffusing solutions comprising:
a container or refill containing the solution to be diffused;
a wick disposed at least partially inside said container to absorb said solution to be diffused;
a heater coupled to said container and to said wick and comprising at least one resistance element, able to increase in temperature when crossed by a current, to heat said wick so as to allow diffusion of said solution from said wick;
supply means able to electrically supply said resistance element;
said resistance element being supported by a support mounted movably in said heater to be able to pass, by user's manual operation, from a position distal to said wick wherein minimum heating of the wick occurs; and
said resistance holding support is in the form of a substantially parallelepiped housing, able to cover at least in part said resistance, leaving the ends of the resistance free for connection to the power supply.

10. A diffuser device according to claim 1, characterised in that said resistance is disposed with the axis at right angles to the axis of the wick.

11. A diffuser apparatus for diffusing solutions comprising:
a container or refill containing the solution to be diffused;
a wick disposed at least partially inside said container to absorb said solution to be diffused;
a heater coupled to said container and to said wick and comprising at least one resistance element, able to increase in temperature when crossed by a current, to heat said wick so as to allow diffusion of said solution from said wick; supply means able to electrically supply said resistance element;
said resistance element being supported by a support mounted movably in said heater to be able to pass, by user's manual operation, from a position distal to said wick wherein minimum heating of the wick occurs; and
said resistance being disposed with its axis parallel to the axis of the wick.

12. A diffuser device according to claim 11, characterised in that said resistance is mounted in a cylindrical resistance holding support integrated in a circular frame integral with an operating flange rotatably mounted inside the heater and disposed around a hole of the operating flange for passage of the wick.

13. A diffuser device according to claim 1, characterised in that terminals of said resistance are connected, by means of electrical wires, to electrical contacts of a plug.

14. A diffuser device according to claim 13, characterised in that said plug is mounted rotatably in said heater around an axis substantially parallel to the axis of the pins of the plug.

15. A diffuser device according to claim 12, characterised in that said burner comprises a lower shell half and an upper shell half that can be coupled together so as to define a chamber wherein said resistance holding support and one end of said wick are disposed.

16. A diffuser device according to claim 15, characterised in that said container or refill is coupled to the lower shell half so that one end of the wick is immersed in the solution contained in the container and in that said upper shell half has at least one through hole or slot for diffusion of the solution towards the outside by said wick.

* * * * *